(12) United States Patent
Rajagopal et al.

(10) Patent No.: US 9,070,733 B2
(45) Date of Patent: Jun. 30, 2015

(54) NANOPILLAR FIELD-EFFECT AND JUNCTION TRANSISTORS WITH FUNCTIONALIZED GATE AND BASE ELECTRODES

(71) Applicants: CALIFORNIA INSTITUTE OF TECHNOLOGY, Pasadena, CA (US); SANOFI, Paris (FR)

(72) Inventors: Aditya Rajagopal, Irvine, CA (US); Chieh-feng Chang, Pasadena, CA (US); Oliver Plettenburg, Frankfurt (DE); Stefan Petry, Frankfurt (DE); Axel Scherer, Barnard, VT (US); Charles L. Tschirhart, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 13/941,295

(22) Filed: Jul. 12, 2013

(65) Prior Publication Data
US 2014/0030819 A1    Jan. 30, 2014

Related U.S. Application Data

(60) Provisional application No. 61/675,637, filed on Jul. 25, 2012.

(51) Int. Cl.
*H01L 29/73* (2006.01)
*H01L 29/78* (2006.01)
(Continued)

(52) U.S. Cl.
CPC ............... *H01L 29/73* (2013.01); *H01L 29/78* (2013.01); *B82Y 15/00* (2013.01); *H01L 29/732* (2013.01);
(Continued)

(58) Field of Classification Search
CPC . B82Y 15/00; G01N 27/414; G01N 27/4141; G01N 27/4145; G01N 27/4146; G01N 27/4148; G01N 27/00; G01N 27/3278; G01N 33/54373; G01N 33/54346; H01L 29/76; H01L 29/772; H01L 29/78
USPC .............. 422/82.01; 435/287.2, 7.1; 977/742, 977/762, 938, 700, 773, 904
See application file for complete search history.

(56) References Cited

U.S. PATENT DOCUMENTS 4,800,556 A    1/1989  Charlier et al.
4,825,081 A    4/1989  Wille
(Continued)

FOREIGN PATENT DOCUMENTS

EP    0053790    6/1982
EP    0386965    9/1990
(Continued)

OTHER PUBLICATIONS

PCT International Search Report mailed on Oct. 15, 2013 for PCT/US2013/050367 filed on Jul. 12, 2013 in the name of California Institute of Technology, 6 pages.
(Continued)

*Primary Examiner* — Melanie Y Brown
*Assistant Examiner* — Erik B Crawford
(74) *Attorney, Agent, or Firm* — Steinfl & Bruno LLP

(57) ABSTRACT

Systems and methods for molecular sensing are described. Molecular sensors are described which are based on field-effect or bipolar junction transistors. These transistors have a nanopillar with a functionalized layer contacted to either the base or the gate electrode. The functional layer can bind molecules, which causes an electrical signal in the sensor.

11 Claims, 6 Drawing Sheets

(51) Int. Cl.

| | |
|---|---|
| B82Y 15/00 | (2011.01) |
| H01L 29/732 | (2006.01) |
| H01L 29/06 | (2006.01) |
| H01L 29/41 | (2006.01) |
| G01N 27/414 | (2006.01) |

(52) U.S. Cl.
CPC .......... *H01L 29/0676* (2013.01); *H01L 29/413* (2013.01); *G01N 27/4145* (2013.01); *G01N 27/4146* (2013.01)

(56) References Cited

U.S. PATENT DOCUMENTS

| | | | |
|---|---|---|---|
| 5,545,980 | A | 8/1996 | Nakamoto |
| 5,561,479 | A | 10/1996 | Lee |
| 5,784,541 | A | 7/1998 | Ruff |
| 6,130,098 | A | 10/2000 | Handique et al. |
| 6,255,976 | B1 | 7/2001 | Watanabe et al. |
| 6,437,554 | B1 | 8/2002 | Atwater |
| 6,475,890 | B1 | 11/2002 | Yu |
| 6,605,519 | B2 | 8/2003 | Lishan |
| 6,754,950 | B2 | 6/2004 | Furukawa et al. |
| 6,836,578 | B2 | 12/2004 | Kochergin et al. |
| 6,963,119 | B2 | 11/2005 | Colgan et al. |
| 7,368,370 | B2 | 5/2008 | Jain et al. |
| 7,598,552 | B2 | 10/2009 | Park |
| 7,692,218 | B2 | 4/2010 | Barron et al. |
| 7,902,015 | B2 | 3/2011 | Ghozeil et al. |
| 7,923,240 | B2 | 4/2011 | Su et al. |
| 7,965,948 | B1 | 6/2011 | Bugash et al. |
| 8,017,938 | B2 | 9/2011 | Gomez et al. |
| 8,114,787 | B2 | 2/2012 | Kruglick |
| 8,154,058 | B2 | 4/2012 | Hwang et al. |
| 2002/0164884 | A1 | 11/2002 | Lishan |
| 2003/0090161 | A1 | 5/2003 | Marlow et al. |
| 2003/0099273 | A1 | 5/2003 | Murry et al. |
| 2006/0145194 | A1* | 7/2006 | Barron et al. ................ 257/213 |
| 2007/0109121 | A1 | 5/2007 | Cohen |
| 2007/0116082 | A1 | 5/2007 | Feve |
| 2007/0187632 | A1 | 8/2007 | Igarashi |
| 2008/0035494 | A1 | 2/2008 | Gomez et al. |
| 2008/0039770 | A1 | 2/2008 | Francis et al. |
| 2008/0063566 | A1 | 3/2008 | Matsumoto et al. |
| 2008/0070354 | A1 | 3/2008 | Jain et al. |
| 2008/0089367 | A1 | 4/2008 | Srinivasan |
| 2008/0308870 | A1 | 12/2008 | Faul et al. |
| 2009/0015141 | A1 | 1/2009 | Wang et al. |
| 2009/0159123 | A1 | 6/2009 | Kothari et al. |
| 2009/0177144 | A1 | 7/2009 | Masmanidis et al. |
| 2009/0321633 | A1 | 12/2009 | Blick et al. |
| 2010/0008666 | A1 | 1/2010 | Kovsh et al. |
| 2010/0019778 | A1 | 1/2010 | Park et al. |
| 2010/0084729 | A1 | 4/2010 | Steinbrueck |
| 2010/0194409 | A1* | 8/2010 | Gao et al. ................ 324/693 |
| 2010/0248209 | A1 | 9/2010 | Datta et al. |
| 2010/0248284 | A1 | 9/2010 | Chen et al. |
| 2010/0268078 | A1 | 10/2010 | Scarantino et al. |
| 2010/0286686 | A1 | 11/2010 | Hancock |
| 2011/0044694 | A1 | 2/2011 | Scherer et al. |
| 2011/0049650 | A1 | 3/2011 | Tiwari et al. |
| 2011/0218490 | A1 | 9/2011 | Ocvirk et al. |
| 2011/0237000 | A1 | 9/2011 | Tey et al. |
| 2011/0248320 | A1 | 10/2011 | Rothberg et al. |
| 2011/0288391 | A1 | 11/2011 | Rao et al. |
| 2012/0161207 | A1 | 6/2012 | Homyk et al. |
| 2012/0256492 | A1 | 10/2012 | Song et al. |
| 2013/0056353 | A1* | 3/2013 | Nemirovsky et al. .......... 204/416 |
| 2013/0207639 | A1 | 8/2013 | Rajagopal et al. |
| 2013/0230063 | A1 | 9/2013 | Kim et al. |
| 2014/0030819 | A1 | 1/2014 | Rajagopal et al. |
| 2014/0070286 | A1 | 3/2014 | Rajagopal et al. |
| 2014/0072993 | A1 | 3/2014 | Rajagopal et al. |
| 2014/0103735 | A1 | 4/2014 | Chang et al. |

FOREIGN PATENT DOCUMENTS

| | | |
|---|---|---|
| EP | 0451992 | 10/1991 |
| JP | 05-243588 | 9/1993 |
| JP | 2001-250967 | 9/2001 |
| JP | 2004-363594 | 12/2004 |
| JP | 2006-266846 | 10/2006 |
| JP | 2006-267477 | 10/2006 |
| KR | 10-1999-0028493 | 4/1999 |
| KR | 10-0781545 | 12/2007 |
| KR | 10-0906270 | 7/2009 |
| KR | 10-2010-0048380 | 5/2010 |
| KR | 1020100065974 | 6/2010 |
| KR | 10-2012-0021683 | 3/2012 |
| WO | 2012-092209 | 7/2012 |

OTHER PUBLICATIONS

PCT Written Opinion mailed on Oct. 15, 2013 for PCT/US2013/050367 filed on Jul. 12, 2013 in the name of California Institute of Technology, 7 pages.

PCT International Search Report mailed on Oct. 1, 2013 for PCT/US2013/050355 filed on Jul. 12, 2013 in the name of California Institute of Technology, 6 pages.

PCT Written Opinion mailed on Oct. 1, 2013 for PCT/US2013/050355 filed on Jul. 12, 2013 in the name of California Institute of Technology, 6 pages.

Walavalkar et al., Tunable Visible and Near-IR Emission from Sub-10 nm Etched Single-Crystal Si Nanopillars, Nano Letters 2010, 10: 4423-4428.

Restriction Requirement mailed on Jul. 7, 2014 issued for U.S. Appl. No. 13/941,240, filed Jul. 12, 2013 in the name of Chieh-Fang Chang et al., 6 pages.

International Search Report issued for PCT/US2010/046220 filed Aug. 20, 2010 in the name California Institute of Technology et al.

Written Opinion issued for PCT/US2010/046220 filed Aug. 20, 2010 in the name California Institute of Technology et al.

International Search Report mailed on May 16, 2013 issued for PCT/US2013/025632 filed Feb. 11, 2013 in the name of California Institute of Technology.

Written Opinion mailed on May 16, 2013 issued for PCT/US2013/025632 filed Feb. 11, 2013 in the name of California Institute of Technology.

International Search Report issued for PCT Application No. PCT/US2013/034297 filed on Mar. 28, 2013 in the name of California Institute of Technology. mail date: Jan. 24, 2014.

Written Opinion issued for PCT Application No. PCT/US2013/034297 filed on Mar. 28, 2013 in the name of California Institute of Technology. mail date: Jan. 24, 2014.

International Search Report issued for PCT Application No. PCT/US2013/034315 filed on Mar. 28, 2013 in the name of California Institute of Technology. mail date: Jan. 28, 2014.

Written Opinion issued for PCT Application No. PCT/US2013/034315 filed on Mar. 28, 2013 in the name of California Institute of Technology. mail date: Jan. 28, 2014.

W. Andre, et al., "Micro-photovoltaic Cells Designed for Magnetotaxis-based Controlled Bacterial Microrobots", IEICE Electronics Express, 2008, 5: 101-106.

M. Fujita, et al., "Continuous wave lasing in GaInAsP microdisk injection laser with threshold current of 40 µA", Electron. Lett., 2000, vol. 36, pp. 790-791.

N. Hempler, et al., "Pulsed pumping of semiconductor disk lasers", Mar. 19, 2007, Optics Express, 15, 6, pp. 3247-3256.

M.D. Henry, et al., "Alumina etch masks for fabrication of high-aspect-ratio silicon micropillars and nanopillars", Nanotechnology, 20, 25 (2009): 255305. Abstract Only.

K. Inoshita, et al., "Fabrication of GaInAsP/InP photonic crystal lasers by ICP etching and control of resonant mode in point and line composite defects", IEEE J. Sel. Top. Quantum Electron, 2003, vol. 9, pp. 1347-1354.

Y. Mo, et al., "Micro-machined gas sensor array based on metal film micro-heater", Sensors and Actuators B, 2001, vol. 79, pp. 175-181.

(56) References Cited

OTHER PUBLICATIONS

A.S. Sadek, et al., "Wiring nanoscale biosensors with piezoelectric nanomechanical resonators", Nano Lett., 2010, vol. 10, pp. 1769-1773.
R. Ushigome, et al., "GaInAsP microdisk injection laser with benzocyclobutene polymer cladding and its athermal effect", Jpn. J. Appl. Phys., 2002, vol. 41, pp. 6364-6369.
S.S. Walavalkar, et al., "Controllable deformation of silicon nanowires with strain up to 24%", Journal of Applied Physics, 107, 12 (2010): 124314-1 to 124315-5.
Restriction Requirement issued for U.S. Appl. No. 12/860,723, filed Aug. 20, 2010 in the name of Axel Scherer et al. mail date: Jul. 31, 2012.
Non-Final Office Action issued for U.S. Appl. No. 12/860,723, filed Aug. 20, 2010 in the name of Axel Scherer et al. mail date: Oct. 24, 2012.
Final Office Action issued for U.S. Appl. No. 12/860,723, filed Aug. 20, 2010 in the name of Axel Scherer et al. mail date: Apr. 16, 2013.
Notice of Allowance mailed on May 12, 2014 for U.S. Appl. No. 12/860,723, filed Aug. 20, 2010 in the name of Axel Scherer et al.
Notice of Allowance mailed on Sep. 12, 2013 for U.S. Appl. No. 12/860,723, filed Aug. 20, 2010 in the name of Axel Scherer et al.
Restriction Requirement mailed on Sep. 20, 2013 issued for U.S. Appl. No. 13/764,620, filed Feb. 11, 2013 in the name of Seheon Kim.
Non-Final Office Action mailed on Feb. 20, 2014 issued for U.S. Appl. No. 13/764,620, filed Feb. 11, 2013 in the name of Seheon Kim.
Final Office Action mailed on Jul. 15, 2014 issued for U.S. Appl. No. 13/764,620 filed Feb. 11, 2013 in the name of Seheon Kim.
Restriction Requirement mailed on Jun. 13, 2014 for U.S. Appl. No. 13/852,476, filed Mar. 28, 2013 in the name of Aditya Rajagopal.
Restriction Requirement mailed on May 27, 2014 for U.S. Appl. No. 13/852,480 filed Mar. 28, 2013 in the name of Aditya Rajagopal.
Notice of Allowance mailed on Jul. 3, 2014 for U.S. Appl. No. 13/852,480, filed Mar. 28, 2013 in the name of Aditya Rajagopal.
Notice of Allowance mailed on Sep. 3, 2014 for U.S. Appl. No. 13/941,240, filed Jul. 12, 2013 in the name of Chieh-Fang Chang et al.
Non-Final Office Action issued for U.S. Appl. No. 14/306,813, filed Jun. 17, 2014 in the name of Axel Scherer et al. mail date: Oct. 2, 2014.
Non-Final Office Action issued for U.S. Appl. No. 14/463,392, filed Aug. 19, 2014 in the name of Aditya Ragjagopal et al. mail date: Oct. 23, 2014.

* cited by examiner

NANOPILLAR FIELD-EFFECT AND JUNCTION TRANSISTORS WITH FUNCTIONALIZED GATE AND BASE ELECTRODES

CROSS REFERENCE TO RELATED APPLICATIONS

The present application claims priority to U.S. Provisional Patent Application No. 61/675,637, filed on Jul. 25, 2012, the disclosure of which is incorporated herein by reference in its entirety.

TECHNICAL FIELD

The present disclosure relates to semiconductor structures for molecular sensing applications. More particularly, it relates to transistors with functionalized gate and/or base electrodes.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
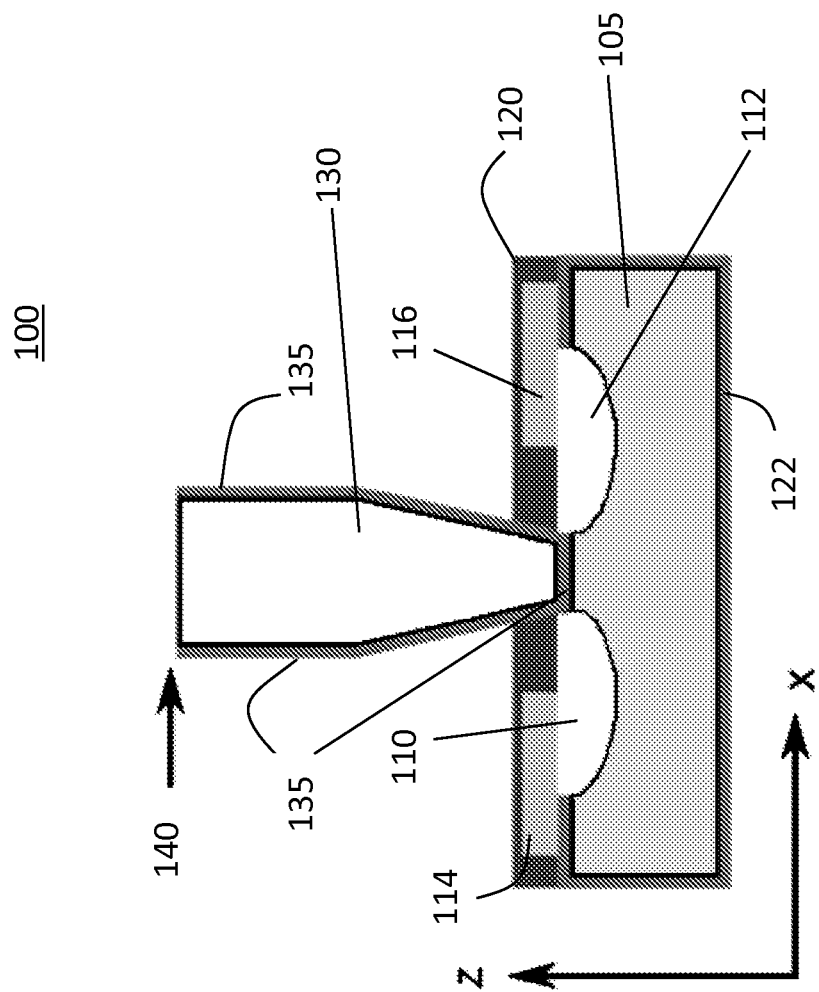
FIG. 1 depicts a cross-section geometry of an exemplary embodiment of a field-effect transistor with a functionalized gate.

According to a first aspect of the disclosure, a structure for sensing molecules is described, the structure comprising: a semiconductor substrate; a source region in the semiconductor substrate, the source region comprising a first doped semiconductor region; a drain region in the semiconductor substrate, the drain region comprising a second doped semiconductor region; a source electrode, contacted to the source region; a drain electrode, contacted to the drain region; an insulating layer, covering at least in part the source electrode, and/or the drain electrode, and/or the source region, and/or the drain region, and/or the semiconductor substrate; an oxide layer, covering a substrate region between the source region and the drain region; a nanopillar gate region, contacting the oxide layer; and a functionalized layer on top of the nanopillar.

According to a second aspect of the disclosure, a structure for sensing molecules is described, the structure comprising: a semiconductor substrate; an emitter region in the semiconductor substrate, the emitter region comprising a first doped semiconductor region; a base region in the semiconductor substrate, the base region comprising a second doped semiconductor region; a collector region in the semiconductor substrate, the collector region comprising a third doped semiconductor region; an emitter electrode, contacted to the emitter region; a collector electrode, contacted to the collector region; a nanopillar, contacting the base region; and a functionalized layer on top of the nanopillar.

According to a third aspect of the disclosure, a structure for sensing molecules is described, the structure comprising: a semiconductor substrate; a source region in the semiconductor substrate, the source region comprising a first doped semiconductor region; a drain region in the semiconductor substrate, the drain region comprising a second doped semiconductor region; a source electrode, contacted to the source region; a drain electrode, contacted to the drain region; an insulating layer, covering at least in part the source electrode, and/or the drain electrode, and/or the source region, and/or the drain region, and/or the semiconductor substrate; a nanopillar gate region, contacting a substrate region between the source region and the drain region; and a functionalized layer on top of the nanopillar.

DESCRIPTION OF EXAMPLE EMBODIMENTS

Described herein are various embodiments in the field of electronics that are directed at the detection of a specific target.

The terms "detect" or "detection" as used herein indicates the determination of the existence, presence or fact of a specific target in a limited portion of space, including but not limited to a sample, a reaction mixture, or other limited portion of space identifiable to a skilled person upon a reading of the present disclosure. The detection can be quantitative or qualitative. A detection is "quantitative" when it refers to, relates to, or involves the measurement of quantity or amount of the target or signal (also referred as quantitation), which includes but is not limited to any analysis designed to determine the amounts or proportions of the target or signal. Detection is "qualitative" when it refers to, relates to, or involves identification of a quality or kind of the target or signal in terms of relative abundance to another target or signal, which is not quantified.

The term "target" as used herein indicates an analyte of interest that is to be detected. The term "analyte" refers to a substance, compound, moiety, or component whose presence or absence in a sample is to be detected. Analytes include but are not limited to molecules and biomolecules. The term "biomolecule" as used herein indicates a substance, compound or component associated with a biological environment including but not limited to sugars, amino acids, peptides, proteins, and oligonucleotides/nucleic acids.

In the field of electronics, transistors have been used as voltage-current and current-current transducers. For molecular sensing applications, it is known that certain molecules bind effectively to metals when those metals are functionalized by chemical and/or biological agents. In some cases, molecules can even bind to metals without any additional layer. In the present disclosure, methods and devices are described, where transistors are actuated by non-electronic means, by functionalizing the terminal contacts of the transistors, for example gate, base, and drain of a MOSFET, with chemical and biological agents. Any number of contacts can be functionalized, from only one to all of them. By functionalizing the gate/base of nanopillar transistors, it is possible to sense biological and chemical targets of interest.

Nano-scale fabrication allows for the fabrication of transistors in various shapes and sizes. For instance, silicon features can be etched in high height:width aspect ratios. Nanopillar structures with aspect ratios ranging from 1:1 to 100:1 can be used to create high surface area contacts. A high surface area contact can be advantageous for molecular sensing applications. These transistors structures can be further shaped to create a variety of three-dimensional geometries. Some geometries can be more efficient at sensing certain molecules, or in specific sensing environments. Nanopillar transistors can be fabricated by standard semiconductor fabrication techniques, commonly known to the person skilled in the art.

In some embodiments, the binding compound for capturing a target for detection can be an antibody. The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof or derivative thereof. The terms "fragment" as used herein with reference to antibody indicates any portion of an antibody that retain an immunogenic activity characteristic of the antibody. The term "derivative" as used herein with reference to an antibody, indicates a molecule that is structurally related to the antibody and is derivable from the antibody by a modification that introduces a feature that is not present in the antibody while retaining functional properties of the antibody. Accordingly, a derivative antibody, or of any fragment thereof, FaB or scFv, usually differs from the original antibody or fragment thereof by modification of the amino acidic sequence that might or might not be associated with an additional function not present in the original antibody or fragment thereof. Methods to provide derivative and to test the ability of the derivative to retain the one or more functional properties are identifiable by a skilled person. Exemplary antibodies include IgA, IgD, IgG1, IgG2, IgG3, IgM and the like. Exemplary fragments include Fab Fv, Fab' F(ab')2 scFV, single chain antibodies and the like. A monoclonal antibody is an antibody that specifically binds to and is thereby defined as complementary to a single particular spatial and polar organization of another biomolecule which is termed an "epitope". In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "binding compound" or "capture agent' as used herein indicates a molecule that can specifically bind to a target, e.g. through the specific binding of one or more of molecule binding sites. Binding compounds herein described can include molecules of various chemical natures such as polypeptides (e.g. antibodies or receptors), polynucleotides (e.g. DNA or RNA) and/or small molecules (e.g. aptamers), as well as other molecules capable of specific binding identifiable by a skilled person upon reading of the present disclosure. In some embodiments, an antibody or antibody fragment can be used to specifically bind or capture a molecule for detection.

In some embodiments the target and/or the binding compound for detection can be a protein or a polynucleotide. The term "protein" as used herein indicates a polypeptide with a particular secondary and tertiary structure that can interact with and in particular bind another analyte and in particular, with other biomolecules including other proteins, DNA, RNA, lipids, metabolites, hormones, chemokines, and small molecules. The term "polypeptide" as used herein indicates an amino acid polymer of any length including full length proteins and peptides, as well as analogs and fragments thereof. A polypeptide of three or more amino acids is also called a protein oligomer, peptide or oligopeptide. In particular, the terms "peptide" and "oligopeptide" usually indicate a polypeptide with less than 50 amino acid monomers. As used herein the term "amino acid", "amino acidic monomer", or "amino acid residue" refers to any of the twenty naturally occurring amino acids, non-natural amino acids, and artificial amino acids and includes both D an L optical isomers.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or with a different functional group. Accordingly, the term "polynucleotide" includes nucleic acids of any length, and in particular DNA, RNA, analogs and fragments thereof.

FIG. 1 illustrates an embodiment of a nanopillar metal-oxide-semiconductor field-effect transistor (MOSFET) with a functionalized gate, which can be used for molecular sensing (100). The semiconductor sensor (100) can be fabricated using standard CMOS fabrication techniques, as well as innovative techniques in pinch-off oxidation and electron-beam annealing of dopants which are known to the person skilled in the art.

The structure (100) of FIG. 1 is fabricated on a semiconductor substrate (105). For example, a silicon substrate can be used, but also other semiconductors can be used as understood by the person skilled in the art. The structure (100) includes a source (110) and a drain (112). The source (110) and drain (112) may be fabricated, for example, by doping the substrate (105). The source (110) and drain (112) can be contacted electrically by electrical interconnects (114) for the source and (116) for the drain. For example, contacts (114) and (116) may be fabricated with metals.

A passivation layer (120) prevents unwanted electrical conduction with contacts (114) and (116). An insulating layer (122) may surround the substrate (105) for insulating purposes. By way of example and not of limitation, the insulating layer (122) may be silicon oxide, for the case of silicon substrates.

The gate structure (130) of the MOSFET sensor can have different geometries. The example of FIG. 1 is intended as exemplary, and other shapes can be used. Different height: width aspect ratios may be used, depending on the application. The gate (130) can be surrounded by an insulating layer (135), for example silicon oxide for the case of silicon substrates.

The structure (100) can comprise a functionalized layer (140). Such layer can have different compositions. It can be a single metallic layer, for example gold, as some molecules are known in the art to functionally bind to gold. Other functionalized layers can be used, which may bind to a wider or narrower range of molecules. Molecules of interest can comprise gases such as nitrogen, as well as biological molecules of interest in biosensing application, such as, for example, polynucleotides or proteins. The functionalized layer (140) can be a single layer, or a composite layer such as a matrix including nanoparticles, or a multiple layer structure, such as a bilayer.

In another example, DNA can be linked to gold or platinum nanoparticles on the functionalized layer and can be used in the specific capture of protein. Procedures can be done to immobilize DNA or RNA to the gold or platinum surface through a thiol linker, as is known to persons skilled in the art. Surface immobilization of nucleic acids can be used as a biosensor assay in order to capture specific nucleic acid binding proteins, or if the nucleic acid that is bound to the layer is single stranded, it can be used to bind its hybridization partner in solution. When target molecules bind to the functionalized layer, the voltage signal caused by the binding of the molecules triggers a signal current in the circuit, as can be understood by the person skilled in the art. The test for specific protein binding can be assayed by using different lengths of the specific DNA bound to the layer in order to verify the binding characteristics of the protein in question.

When a target molecule binds to the functionalized layer (140), an electric charge is induced in the gate (130), leading to the formation of an inversion channel underneath the gate oxide (135). The gate oxide (135) electrically insulates the gate (135) from the substrate (105), the source (110) and the drain (112). The mechanism leading to a formation of an inversion channel underneath the gate (135) mimics the standard mode of operation of MOSFETs, which is well known to the person skilled the art.

By modulating the concentration of a target molecule at the functionalized layer (140) of gate (130), it is possible to transduce a range of currents from the source (110) to the drain (116). In this way, it is possible to detect and amplify concentrations of target molecules in an analyte of interest. Therefore, it can be possible, for example, to detect concentrations of molecules in a liquid, or gas.

Figure 2:
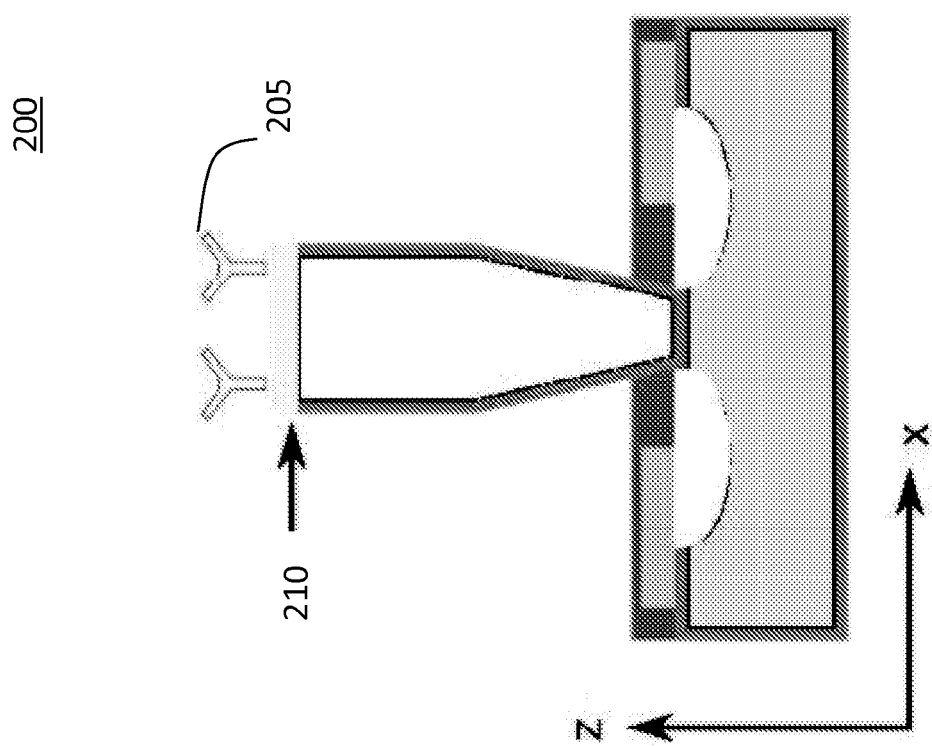
FIG. 2 depicts an exemplary embodiment of a MOSFET with antibodies bound to the functionalized gate.

FIG. 2 illustrates an exemplary embodiment of the structure of FIG. 1 with an antibody-functionalized layer on the gate. Antibodies (205) are bound to the functionalized gate electrode (210).

Figure 3:
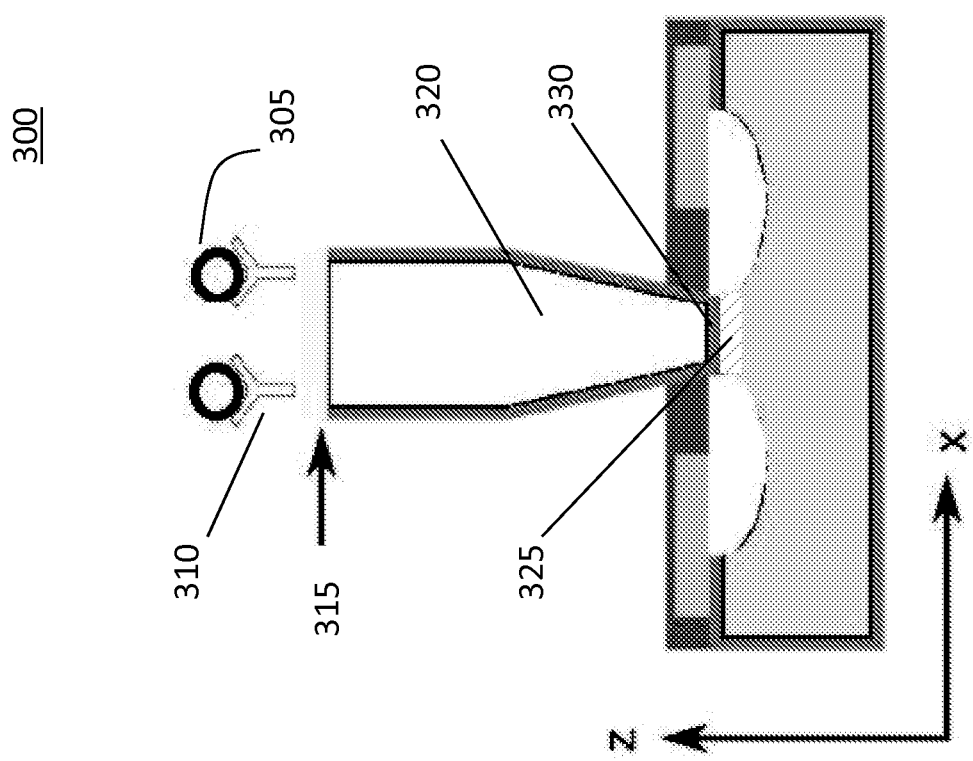
FIG. 3 depicts an exemplary embodiment of a MOSFET with antigens bound to antibodies on the functionalized gate.

FIG. 3 illustrates an exemplary embodiment of antigen capture. An antigen (305) binds to an antibody (310) on the functionalized layer (315). When an antigen (305) binds to an antibody (310) on the functionalized layer (315), an electric charge is induced in the gate (320), leading to the formation of an inversion channel (325) underneath the gate oxide (330). Through such method, an electrical signal is triggered through the formation of an inversion channel (325) in the MOSFET, which is associated with the binding of molecules on the functionalized layer (315).

Figure 4:
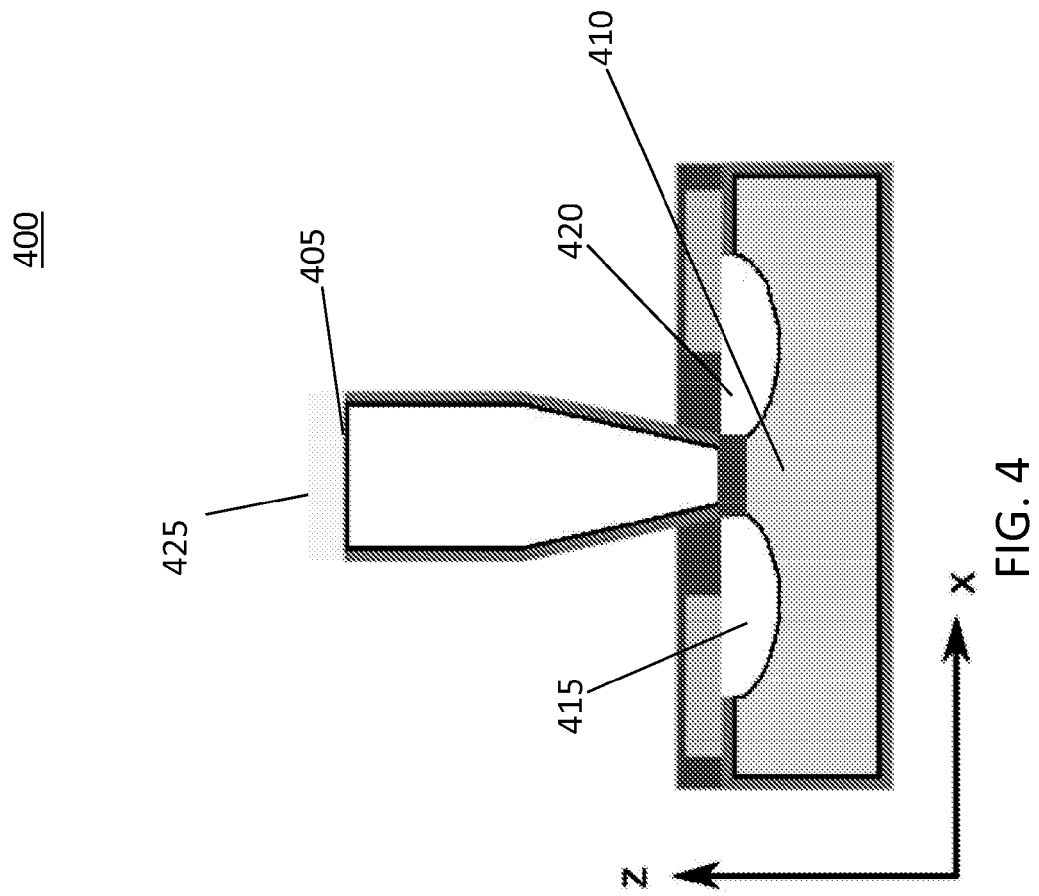
FIG. 4 depicts an exemplary embodiment of a jFET sensor.

FIG. 4 illustrates another exemplary embodiment, where the nanopillar transistor (400) has no gate oxide. In this embodiment, an electric field between the pillar head (405) and the substrate (410) can modulate the current from the source (415) to the drain (420). As it is known to the person skilled in the art, this mode of operation mimics a junction field effect transistor (jFET). Such a transistor can be functionalized, through a functionalized layer (425), with biological and chemical agents for target detection, similarly to the other embodiments of this disclosure.

Figure 5:
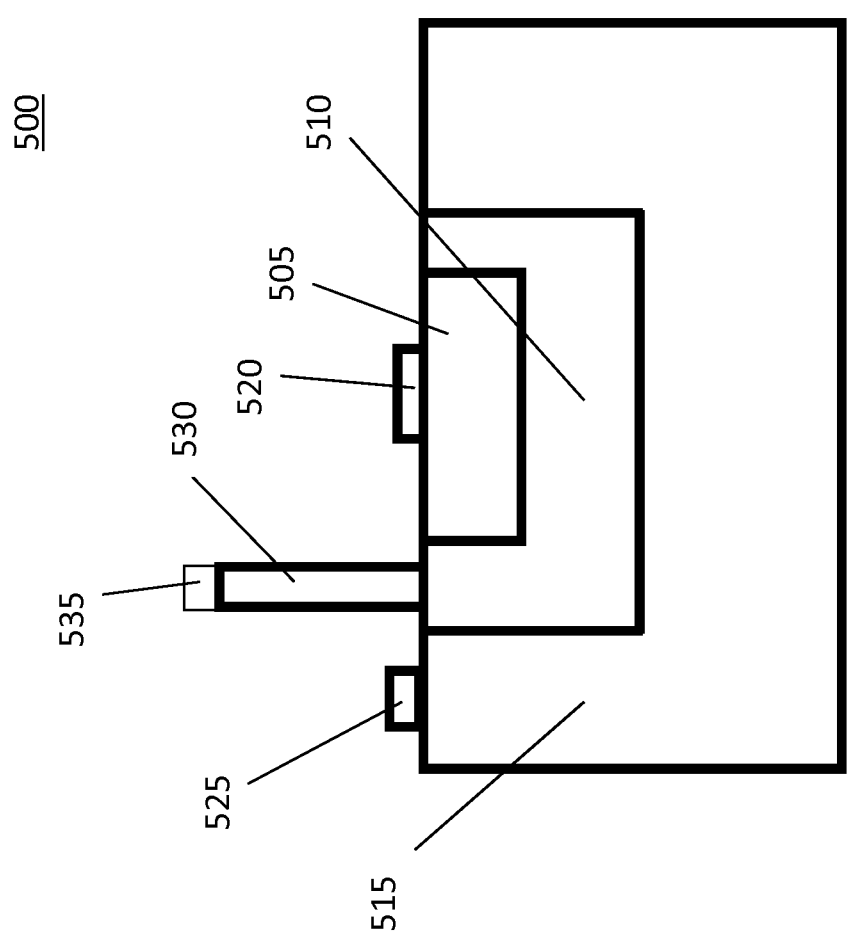
FIG. 5 depicts an exemplary embodiment of a BJT sensor.

FIG. 5 illustrates a further exemplary embodiment, where the sensor (500) is based on a nanopillar bipolar junction transistor (BJT) with a functionalized base electrode. In this configuration, the emitter (505), base (510) and collector (515) form a bipolar junction transistor, as known by the person skilled in the art. For example, the emitter (505) can be an n-doped semiconductor, the base (510) can be a p-doped semiconductor, and the collector (515) can be an n-doped semiconductor. The emitter is electrically contacted by a contact (520), for example a metal, while the collector is contacted by a contact (525). A nanopillar (530) is contacted to the base (510). A functionalized layer (535) can be present on top of the nanopillar (530). The functionalized layer can operate similarly to the other embodiments of the disclosure, such as in FIG. 3. The functionalized layer (535) can be fabricated on top of the nanopillar (530), or on the sides. The nanopillar can have different shapes, not limited to rectangular, cylindrical and tapered. When a target molecule is captured by the functionalized layer (535), a current is injected into the base region (510), which can cause the BJT to operate in forward active conduction. Therefore, an electrical signal is associated with the presence of specific target molecules on the functionalized layer (535).

In the embodiments described in the disclosure, an electrode triggers an electrical signal when a molecule is captured by a functionalized layer, such as layer (535) in FIG. 5, or layer (315) in FIG. 3. This electrode can be composed of a variety of materials, including (but not limited to), silicon, silicon oxide, sapphire, aluminum, copper, rhodium, gallium, palladium, platinum, iridium, Ag—AgCl, and gold. Proper selection of electrode material will allow for selective binding of chemical and biological agents to the target molecules, allowing for electrical detection of target molecules of interest. Alternatively, the gate electrode material can be used to directly facilitate electrochemical reactions on its surface. For example, Pt—PtRu gate contacts can be used to characterize methanol oxidation/reduction.

The method described in the disclosure can be extended to allow for other types of detection. For example, bonding of chemical and biological agents to the functionalized layers described in the disclosure can be used for detection of different target molecules, including (but not limited to), hydrocarbon groups for glucose detection, hydrocarbon membranes for methanol detection, and chemical structures for $H_3O^+$ and $H^+$ detection.

In other embodiments, the functionalized layer comprises chi-selective and epsilon-selective materials. The method of the disclosures can be further used for magnetic and electrical detection of a variety of target molecules (e.g. hemoglobin, DNA).

In one embodiment, a configuration of a nanopillar MOSFET transistor involves the functionalization of the gate electrode with monoclonal antibodies. These antibodies are bound to the gate electrode using epoxide chemistries. When the antigen capture occurs, there will be a conformational change in the structure of the antibody. This conformational change, in conjunction with the proximity of the target antigen to the gate, induces a charge in the gate electrode. This charge creates a channel below the gate oxide, turning ON the MOSFET.

By way of example and not of limitation, the antibodies attached to the functionalized layer of FIG. 2 and FIG. 3 can also be used to indirectly capture targets by initially being bound to a specific antigen that is specific for binding a particular molecule. The antigen that is specific for binding a particular molecule can have multiple binding sites that are not affected in binding a specific molecule when it is bound to the antibody on the functionalized layer. Said molecule of interest can be a specific nucleic acid sequence, such as one of DNA or RNA sequence, or a particular protein of interest. When the antigen that is bound to the antibody captures a specific molecule of interest, a conformational change occurs in the structure of the antigen that is translated to the bound antibody, thus inducing a charge in the gate electrode, thereby creating a channel below the gate oxide, turning ON the MOSFET. By way of example and not of limitation, a DNA binding protein such as a transcription factor can be bound to the antibody in order to capture a specific DNA sequence.

Figure 6:
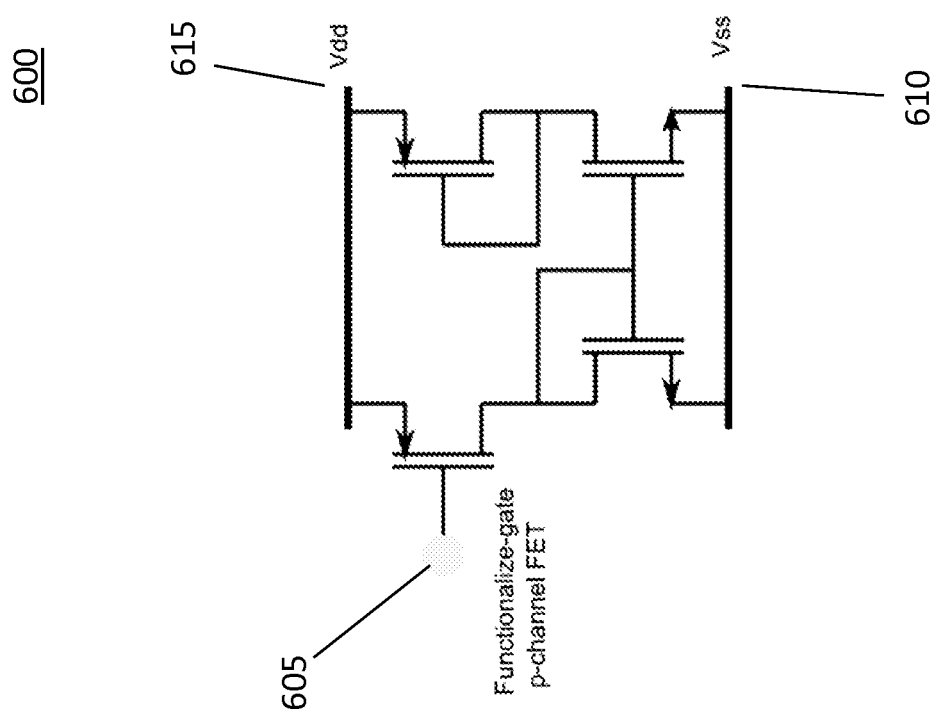
FIG. 6 depicts an exemplary embodiment of a circuit to sense the signal from a field-effect transistor sensor.

The fabrication of the nanopillar transistors can be completely CMOS compatible, a clear advantage as known to the person skilled in the art, as it allows for the integration of the functionalized transistors with conventional transistors on a single semiconductor substrate. For instance, a functionalized nanopillar FET can be contacted with CMOS transistors to code for a small signal gate voltage into a large signal current. An exemplary circuit to realize this embodiment is illustrated in FIG. 6. In FIG. 6, a functionalized-gate p-channel field effect transistor (605) is shown. A source voltage (610) and drain voltage (615) are provided for the operation of circuit (600).

When target molecules bind to the functionalized layer of transistor (605), the voltage signal caused by the binding of the molecules triggers a signal current in the circuit (600), as can be understood by the person skilled in the art. Since the nanopillar transistors can be compatible with CMOS fabrication techniques, a monolithic integration of functionalized transistors with conventional electronics on single semiconducting substrate is possible.

The examples set forth above are provided to those of ordinary skill in the art a complete disclosure and description of how to make and use the embodiments of the gamut mapping of the disclosure, and are not intended to limit the scope of what the inventor/inventors regard as their disclosure.

Modifications of the above-described modes for carrying out the methods and systems herein disclosed are obvious to persons of skill in the art and are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A structure for sensing molecules, the structure comprising:
   a semiconductor substrate;
   a source region in the semiconductor substrate, the source region comprising a first doped semiconductor region;
   a drain region in the semiconductor substrate, the drain region comprising a second doped semiconductor region;
   a source electrode, contacted to the source region;
   a drain electrode, contacted to the drain region;
   a first insulating layer, covering at least in part one or more of the source electrode, the drain electrode, the source region, the drain region, and the semiconductor substrate;
   a nanopillar, covered by a second insulating layer on bottom and lateral areas of the nanopillar and formed between the source region and the drain region; and
   a functionalized gate electrode on a top area of the nanopillar.

2. The structure of claim 1, wherein the shape of the nanopillar is a cylindrical shape.

3. The structure of claim 1, wherein the functionalized gate electrode comprises two layers, or a matrix layer containing nanoparticles.

4. The structure of claim 1, wherein the functionalized gate electrode is made from a material selected from a group consisting of silicon, silicon oxide, sapphire, aluminum, copper, rhodium, gallium, palladium, platinum, iridium, Ag—AgCl, gold, and Pt—PtRu.

5. The structure of claim 1, wherein the nanopillar is configured to directly facilitate electrochemical reactions on its surface.

6. The structure of claim 1, wherein the functionalized gate electrode comprises antibodies for antigen capture.

7. The structure of claim 1, wherein the functionalized gate electrode can bind to molecules, wherein the molecules comprise chemical and biological molecules.

8. The structure of claim 7, wherein the biological molecules comprise DNA.

9. A method for detecting molecules with the structure of claim 1, the method comprising:
   providing a gas and/or fluid solution;
   contacting the solution to the functionalized gate electrode;
   detecting the molecules based on an electrical signal between the source region and the drain region.

10. The structure of claim 1, wherein the shape of the nanopillar is a rectangular shape.

11. The structure of claim 1, wherein the shape of the nanopillar is a tapered shape.

* * * * *